(12) United States Patent
Einfalt et al.

(10) Patent No.: US 10,806,393 B2
(45) Date of Patent: Oct. 20, 2020

(54) SYSTEM AND METHOD FOR DETECTION OF COGNITIVE AND SPEECH IMPAIRMENT BASED ON TEMPORAL VISUAL FACIAL FEATURE

(71) Applicant: FUJI XEROX CO., LTD., Minato-ku, Tokyo (JP)

(72) Inventors: Moritz Werner Amadeus Einfalt, Augsburg (DE); Lyndon Kennedy, San Francisco, CA (US); Matthew Len Lee, Mountain View, CA (US); Rainer Wolfgang Lienhart, Friedberg (DE); Lynn Donelle Wilcox, Redwood City, CA (US)

(73) Assignee: FUJI XEROX CO., LTD., Tokyo (JP)

( * ) Notice: Subject to any disclaimer, the term of this patent is extended or adjusted under 35 U.S.C. 154(b) by 127 days.

(21) Appl. No.: 16/261,350

(22) Filed: Jan. 29, 2019

(65) Prior Publication Data
US 2020/0237290 A1   Jul. 30, 2020

(51) Int. Cl.
| | |
|---|---|
| *A61B 5/00* | (2006.01) |
| *G10L 25/66* | (2013.01) |
| *G06K 9/00* | (2006.01) |
| *G06K 9/62* | (2006.01) |
| *A61B 5/11* | (2006.01) |

(52) U.S. Cl.
CPC ......... *A61B 5/4803* (2013.01); *A61B 5/1114* (2013.01); *A61B 5/7275* (2013.01); *G06K 9/00268* (2013.01); *G06K 9/00718* (2013.01); *G06K 9/6218* (2013.01); *G06K 9/6269* (2013.01); *G10L 25/66* (2013.01)

(58) Field of Classification Search
CPC ............. A61L 35/4803; A61L 35/7275; A61L 35/1114; G06K 9/6218; G06K 9/00268; G06K 9/6269; G06K 9/00718
See application file for complete search history.

(56) References Cited

U.S. PATENT DOCUMENTS

| | | | |
|---|---|---|---|
| 5,687,280 A | * 11/1997 | Matsui ............... | G06K 9/00268 704/231 |
| 10,382,722 B1 | * 8/2019 | Peters .................... | H04N 7/152 |

(Continued)

OTHER PUBLICATIONS

Cao et al. "Realtime Multi-Person 2D Pose Estimation using Part Affinity Fields" In IEEE CVPR, Jul. 2017; 9 pages.

(Continued)

*Primary Examiner* — John B Strege
(74) *Attorney, Agent, or Firm* — Procopio, Cory, Hargreaves & Savitch LLP

(57) ABSTRACT

A computer-implemented method of assessing whether a patent has a condition is provided, including generating a facial landmark on a received input video to define points associated with a region of interest on a face of the patient, defining a period of talking based respective positions of the defined points, during the period of talking, measuring pause frequency, repetitive pattern, and vocabulary variety, without determining or applying semantic information associated with the talking, to generate an aggregate score, and based on the aggregate score, generating a prediction of the patient having the condition associated with the aggregate score.

20 Claims, 7 Drawing Sheets
(4 of 7 Drawing Sheet(s) Filed in Color)

(56) References Cited

U.S. PATENT DOCUMENTS

2014/0201126 A1* 7/2014 Zadeh .................... A61B 5/165
  706/52
2014/0379351 A1* 12/2014 Raniwala ........... G06K 9/00335
  704/270
2017/0195637 A1* 7/2017 Kusens ................ G06K 9/4604

OTHER PUBLICATIONS

Cherney, L. "Oral Reading for Language in Aphasia (ORLA): Evaluating the Efficacy of Computer-Delivered Therapy in Chronic Nonfluent Aphasia" Topics in Stroke Rehabilitation, Nov.-Dec. 2010; 10 pages, 17(6); Thomas Land Publishers, Inc.

Goodall, C. "Procrustes Methods in the Statistical Analysis of Shape" Journal of the Royal Statistical Society. Series B (Methodological), 1991, 56 pages; vol. 53, No. 2.

Keogh, E. et al. "Scaling up Dynamic Time Warping for Datamining Applications" In Proceedings of the sixth ACM SIGKDD, 2000, 5 pages; Boston, MA.

MacWhinney, B. et al. "Aphasiabank: Methods for Studying Discourse" Aphasiology, Sep. 22, 2011; 23 pages; vol. 25, Issue 11.

Martinez, B. et al. "Automatic Analysis of Facial Actions: A Survey" Journal of LATEX Class Files, Sep. 2014; 22 pages, vol. 13, No. 9.

Niinuma, K. et al. "Automatic Multi-view Face Recognition via 3D Model Based Pose Regularization" IEEE 6th International Conference on Biometrics: Theory, Applications and Systems (BTAS), Sep. 29-Oct. 2, 2013, 8 pages; Washington DC, USA.

Petridis, S. et al. "End-to-End Visual Speech Recognition with LSTMS" In IEEE ICASSP, Mar. 2017; 5 pages.

Sakoe, H. et al. "Dynamic Programming Algorithm Optimization for Spoken Word Recognition" IEEE Transactions on Acoustics, Speech, and Signal Processing, Feb. 1978, 7 pages; vol. ASSP-26, No. 1; Elsevier.

Varchmin, A. et al. "Image Based Recognition of Gaze Direction Using Adaptive Methods" In Gesture and Sign Language in Human-Computer Interaction, 1998; 13 pages; Springer Berlin Heidelberg.

Wang, J. et al. "Video-Based Emotion Recognition using Face Frontalization and Deep Spatiotemporal Feature" In 2018 First Asian Conference on Affective Computing and Intelligent Interaction (ACII Asia); May 1-6, 2018; 6 pages.

* cited by examiner

200

_300_

SYSTEM AND METHOD FOR DETECTION OF COGNITIVE AND SPEECH IMPAIRMENT BASED ON TEMPORAL VISUAL FACIAL FEATURE

BACKGROUND

Field

Aspects of the example implementations relate to methods, systems and user experiences associated with detecting speech and cognitive impairment based on a video sequence while using only visual facial features and without detecting content of the speech of the user.

Related Art

Individuals (e.g., patients) with neurological conditions may experience speech impairment as a symptom of those neurological conditions. For example, aphasia is a neurological condition that affects the ability of an individual to comprehend or produce speech. Aphasia may result from a stroke or other brain injury, and may improve or worsen over time. The degree and type of speech impairment associated with aphasia may span across a broad continuum. For example, an individual having aphasia may have slightly dysfluent speech (e.g., pause, repeating of words, or having limited vocabulary), or severe limitations that only allow few words or utterances.

In the related art, assessment of the abilities of individuals with aphasia may be performed. According to one related art, approach a doctor or therapist may perform a manual determination of aphasia. The related art assessment may range from a broad classification of the capability of a patient up to a detailed analysis of symptoms based on clinical interview transcripts. For example, in the case of a medical professional using clinical interview transcripts to analyze symptoms associated with aphasia, a great deal of time is required, and the result may not be representative of the abilities of the patient outside of the clinical environment, as the patient may not react in the same way in a clinical setting and in a non-clinical setting.

Related art assessment may have errors. Further, the interview transcripts may reveal speech content, such as private information or sensitive content, which exposes private information of the user. Thus a user may have to either risk compromising private information to the clinician or others, or not obtaining therapy or treatment for aphasia.

According to one related art approach, audio information may be used to infer speech capabilities. However, an audio approach would require the system to detect the content of the conversation of the patient. Such an approach can cause related art problems about the disclosure of confidential information, as well as the privacy of the patient.

Thus, there is an unmet need to permit assessment of a patient's capabilities over time in a privacy preserving and confidentiality preserving manner, which also avoids the related art errors associated with the analysis being performed in the clinical environment.

SUMMARY

According to aspects of the example implementations, a computer-implemented method of assessing whether a patient has a condition is provided, comprising generating a facial landmark on a received input video to define points associated with a region of interest on a face of the patient, defining a period of talking based respective positions of the defined points, during the period of talking, measuring pause frequency, repetitive pattern, and vocabulary variety, without determining or applying semantic information associated with the talking, to generate an aggregate score; and based on the aggregate score, generating a prediction of the patient having the condition associated with the aggregate score.

According to another aspect, the generating the facial landmark comprises defining, for the region of interest comprising the mouth of the patient, the defined points outlining the lips of the patient, and measuring, over time, a temporal similarity measure of the defined points, and removing body movement and head movement from the temporal similarity measure to generate a temporal dissimilarity measure for the mouth.

According to yet another aspect, the defining the period of talking comprising filtering out mouth movement associated with jitter and out-of-plane rotations of the mouth, measuring a vertical distance between an upper lip and a lower lip of the lips, and performing a closing operation to generate a talk score indicative of the period of talking.

According to still another aspect, the measuring the pause frequency comprising applying a threshold to the talk score, and registering periods of talk inactivity during the period of talking as the pause frequency.

According to an additional aspect, the measuring the repetitive pattern comprising defining first and second patterns of mouth motion during the period of talking having a length around respective first and second time intervals, and performing a dissimilarity comparison to obtain a number of repetitions over a time period.

According to a further aspect, the measuring the vocabulary variety comprising collecting and aggregating a fixed number of vocabulary patterns throughout the input video using clustering with a fixed number of clusters by selecting repeating ones of the patterns, reconstructing the mouth motion over the fixed number of vocabulary patterns to generate a reconstruction cost indicative of a score of mouth motion variety.

According to a still further aspect, the vocabulary variety is measured without identifying a language of the vocabulary.

According to another aspect, the generating the prediction further comprises applying a decision tree or a support vector machine to learn a separating function between the patient having the condition and the patient not having the condition.

Example implementations may also include a non-transitory computer readable medium having a storage and processor, the processor capable of executing instructions for assessing whether a patent has a condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
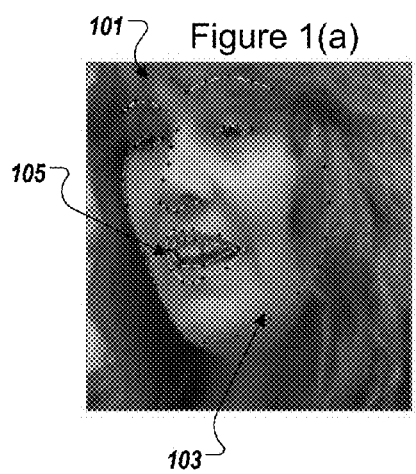
FIGS. 1(a)-1(d) illustrate an example implementation of the incoming feature image with facial landmarking, and measurements according to various example implementations.

The following detailed description provides further details of the figures and example implementations of the present application. Reference numerals and descriptions of redundant elements between figures are omitted for clarity. Terms used throughout the description are provided as examples and are not intended to be limiting.

There is an unmet need for automated assessment tools that track speech abilities more frequently over time, as well as outside of the clinical environment. Such an approach would permit more effective tailoring of therapy for people with aphasia, or other cognitive and speech impairments. According to one approach, assessment tools may be integrated with every day video calls to provide a more continuous and representative evaluation of speech impairments, and to detect improvement or worsening over time.

Aspects of the example implementations are directed to methods and systems for detection of speech and cognitive impairments based on video sequences. More specifically, a cross-media approach is employed, that applies only visual facial features to detect speech properties, without using the audio content of the speech. For example, facial landmark detection results may be used to measure facial motion over time. Accordingly, speech and pause instances are detected based on temporal mouth shape analysis, and identification of repeating mouth patterns, using a dynamic time warping mechanism. In one example implementation, the above-noted features associated with pause frequency, mouth pattern repetition, and vocabulary pattern variety are applied to detect symptoms associated with a medical condition such as aphasia.

Computer vision is employed to model conditions that are related to speech and cognition. In contrast to related art approaches of tracking facial points to recognize, identify or detect facial gestures such as gaze or emotion, the example implementation is directed to modeling speech and cognition. Further, and also distinguishable from related art audio/visual speech recognition using visual signals to directly transcribe the words being spoken by the patient, the example implementations characterize properties of speech, such as pace of words, the degree to which motions are repetitive, and the variety of vocabulary employed, without revealing the content of the speech itself, to infer the existence of a condition, such as aphasia.

According to the example implementations described herein, the cross-media approach only uses visual information to infer speech-related properties, such that the privacy of the patient is protected, by not detecting or determining the semantic content of their speech. Further, the privacy protecting approach of the example implementations may increase acceptance of automatic evaluation systems, and provide for further possible implementations with respect to diagnosis and therapy. Additionally, the example implementations may provide for continuous assessment of patient capabilities during video conferences or specific discourses with medical professionals, self-evaluation over time by the patient, or aggregation, with the consent of the patient, for large-scale medical studies.

According to the example implementations, for a patient having capabilities assessed with respect to aphasia, initial registration of facial landmarks is performed while the patient is speaking. Based on the initial registration of the facial landmarks associated with the face of the patient, temporal features for speech and pause detection are developed, as well as detection of repeating facial patterns, and measurement of overall facial pattern variety, directly based on the facial landmarks. Further, the temporal features are associated with actual speech related symptoms of patients with aphasia, including but not limited to dysfluency, repetitive speech, and use of a limited vocabulary.

In more detail, the example implementations are directed to analysis of the mouth of the patient, and more specifically, to shapes and motion of the mouth, so as to develop features that are related to actual speech properties. Point detections that outline the mouth of the patient in a received video, and compare their shape over time are employed. Such point detections may reveal speaking turns, as well as short pauses within speaking turns. Further, temporally sequential mouth shapes are grouped into mouth patterns, and different patterns are compared with each other, to identify repeating patterns that occur during talking by the patient. Additionally, variety in mouth motion is measured for the patient, by comparing the patterns to a small vocabulary of observed patterns.

According to the example implementations, an incoming video sequence of a patient, such as a patient speaking, is used as the starting data. For this video sequence, 2-D landmarks are registered. The example implementation employs an approach that uses convolutional neural networks to obtain a 70 point model for the characteristic facial points. While 70 points are used in the example shown herein, the example implementations are not limited thereto and any number of points associated with the characteristics of a face may be used as would be understood by those skilled in the art.

For example, FIG. 1(a) illustrates a phase 101 of a patient having facial points 103, showing a frame of the incoming video sequence. As would be understood by those skilled in the art, the facial points are obtained using well-known, off the shelf software executed on a processor, such as a GPU or CPU. A substantial proportion of the facial points do not change during speech by the patient in a manner that is meaningful with respect to the analysis of the patient's capabilities for aphasia. Accordingly, the example implementations focus on a subset of the facial points that are associated with change that occurs during speaking by the patient. These points are shown in FIG. 1(a) at 105 as the points associated with internal and external lip features of the lip of the mouth. For example, in the case where there are 70 facial points, the facial points outlining the lips, such as roughly 20 facial points, may be used for the analysis. While the foregoing numbers and proportions are provided for example purposes, the present inventive concept is not limited to these parameters, and other parameters may be used as would be understood by those skilled in the art.

Accordingly, the set of 2-D facial points that meaningfully change when the patient is speaking, at a specific point in time t of the video, are represented as shown below in equation (1):

$$m_t = \begin{pmatrix} x_1 & x_2 & \ldots & x_M \\ y_1 & y_2 & \ldots & y_M \end{pmatrix} \quad (1)$$

Further, it is noted that the video material may be normalized to a standard rate, such as 30 frames per second. Accordingly, any point in time t may be specified by a frame index.

The analysis of mouth configurations, and the motion thereof over time, is based on a temporal similarity measure of the 2-D facial points, such as mouth, associated with the patient, as well as direct measurements of the prescribed facial features, such as opening of the mouth. To compare how much the shape of a mouth changes over time, a measurement is taken with respect to a difference between two mouth configurations, based on their point wise quadratic difference, for example as shown below in equation (2):

$$\|m_{t1} - m_{t2}\|_2^2 \quad (2)$$

Figure 1B:
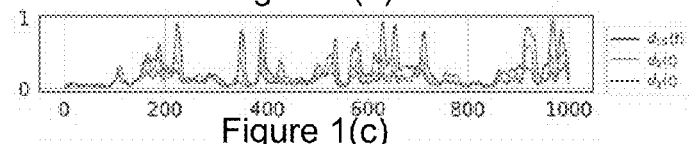

Changes in mouth configuration over time may result from body movement, head movement or inner-facial motion. In order to consider the changes based on inner-facial motion, arbitrary scaling, 2-D rotation and translation are performed to map one of the compared mouth configurations as closely as possible onto another of the mouth configurations, and to use the remaining difference to represent an actual difference in shape. Further, the example implementations directly map multiple mouth configurations to be compared without requiring an intermediate mapping onto a frontal template view of the mouth. Because the information of interest is the difference of temporally nearby mouth configurations in a video, the example implementation avoids additional error that may be induced by related art approaches that use frontalization. For example, FIG. 1(b) shows temporal mouth dissimilarity for different temporal windows. Thus, the example implementations provide for shape analysis by providing the mouth dissimilarity measures shown in equation (3):

$$msim(m_{t1}, m_{t2}) = \min_{s,\theta,t} \|m_{t1} - sR_\theta m_{t2} + t\|_2^2. \quad (3)$$

Because msim depends on the scale of the first operand, asymmetric and scale invariant function is provided as follows in equation (4):

$$msim_{norm}(m_{t1}, m_{t2}) = \frac{msim(m_{t1}, m_{t2})}{s_{m_{t2}}} + \frac{msim(m_{t2}, m_{t1})}{s_{m_{t2}}} \quad (4)$$

Accordingly, $msim_{norm}$ is used to measure or inner-facial motion, by comparing mouth configurations of the patient in a temporal window $\Delta t$. To account for the determination as to which $\Delta t$ value will provide optimal measure, a collection of different temporal windows W is employed. Accordingly, the final temporal self-dissimilarity measure for the mouth is provided as shown in equation (5):

$$d_w(t) = \sum_{\Delta t \in w} msim_{norm}(m_t, m_{t+\Delta t}) \quad (5)$$

The foregoing operations are performed as instructions stored in a storage and executed as operations on a processor, such as a GPU or CPU. Once the 2-D landmarks on the face of the patient have been registered using a model such as the one described above in the foregoing example implementations, analysis of the condition of the patient with respect to speech capabilities may be performed, such as talking detection, pause frequency and repetitive pattern analysis, for example with respect to aphasia.

The example implementations provide for detection of when the patient is talking in the time window of the received input video, to infer different properties of the speech capabilities of the patient. Talking occurs when the mouth is open and moving, and results in mouth movement, such that periods of talking are revealed as areas of high activity (e.g., dissimilarity) in equation (5), for example, which captures mouth movement during talking, as well as jitter in the point detections or missed detections, and changes due to out of plane rotations of the mouth, such as when the patient is nodding or shaking his or her head. To account for jitter, the time instances where all facial landmarks are detected with sufficient confidence is required.

To account for the changes due to out of plane rotations of the mouth such as nodding or shaking the head, the registration errors that occur in such a circumstance are filtered based on talking only being able to occur when the mouth is open at some point during the window. For example, the vertical distance between points on the upper and lower lips may be measured, such as using o(t) as the vertical opening of the inner mouth, normalized by the scale of the complete face. It is noted that o(t) will change frequently during talking, and thus a closing operation may be applied, to smooth over gaps for up to $\Delta t = 50$, with a combined minimum and maximum filter, so as to obtain the vertical distance as follows in equation (6):

$$o_{max}(t) = \min\left(\max_{t' \in [t-\Delta t, t]} o(t), \max_{t' \in [t, t+\Delta t]} o(t)\right) \quad (6)$$

Figure 1C:
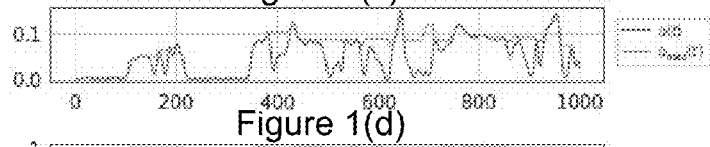

As shown in FIG. 1(c) above, on a sample video, o(t) and $o_{max}(t)$ are shown across the time window. The gaps of a briefly closed mouth during talking are filled, while retaining sharp boundaries for periods of non-talking. Accordingly, a threshold value of $o_{max}(t)$ may be defined as a precondition to establish that talking has been detected. Further, had motion without talking or mouth opening is filtered out, such as when a person is simply nodding. The final talk score (e.g., mouth movement times mouth openness) is provided as shown below in equation (7):

$$\text{talk}(t) = d_w(t) \cdot o_{max}(t) \quad (7)$$

Figure 1D:
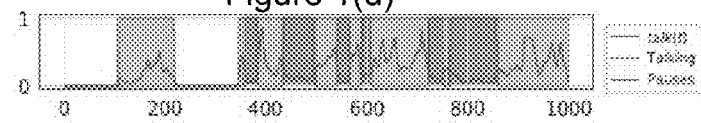

Further, the self-dissimilarity measure of the mouth as described above with respect to equation (5) and the vertical distance measurement as defined above with respect to equation (6) our maximum-normalized to [0, 1]. Additionally, a talk threshold $\tau_{talk}$ may be employed for a hard {0, 1} assignment, and very short talking intervals may be removed, and further, closely adjacent talking intervals that are separated only by very short gaps may be joined, so as to generate a talk instance detection, as shown in FIG. 1(d). The foregoing operations are performed as instructions stored in a storage and executed as operations on a processor, such as a GPU or CPU.

Once a determination can be made as to whether the patient is talking, pause frequency may be determined. For example, for a patient with aphasia, dysfluent speech, manifested as unintended pauses during talking, is a decisive symptom. Thus, example implementations are directed to developing a measure for pauses as a direct measure of fluency. In the example implementations, pauses are detected by using the talk score as explained above with respect to equation (7), and then applying a more restrictive threshold $\tau_{pause}$, and also registering all areas of inactivity during previously detected talk instances. The foregoing operations are performed as instructions stored in a storage and executed as operations on a processor, such as a GPU or CPU.

As explained above, FIG. 1(d) illustrates an example of such pauses during periods of talking. Although pauses that are intentionally provided by the patient as a normal course of speaking are provided, the overall pause frequency can still be correlated with respect to the speech fluency of the patient.

Figure 2A:
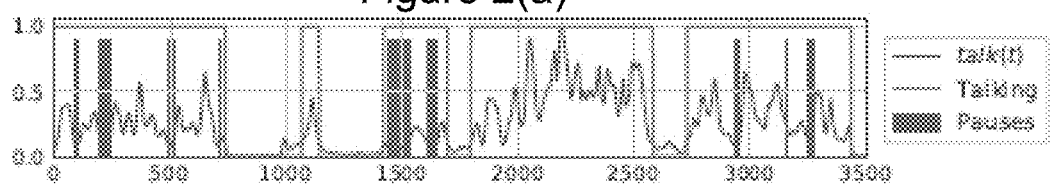
FIGS. 2(a)-2(b) illustrate a comparison of pauses for a person with aphasia and a control group member, as determined according to an example implementation.
Figure 2B:
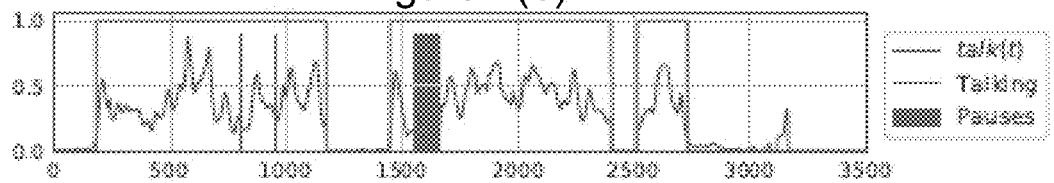

As shown in FIGS. 2(a) and 2(b) respectively, a qualitative example may be provided that shows the difference in pause frequency for a person with aphasia, as compared with a control group member.

In addition to dysfluent speech, aphasia patients also have a characteristic of frequent repetitions of utterances, words or sentence fragments. These repetitions can occur when forming the next word, or trying to correct the previous word. The example implementations are directed to detecting repetitions in the mouth motion that are related to speech repetitions. Although repeating mouth motion may not indicate repetition with respect to the semantics of the content of the speech, information associated with visual representation can be determinative of repetition behaviors.

To detect a visual repetitions of mouth motion, a pattern of mouth motion having a length of l around a time t are defined in equation (8):

$$p_t = (m_{t-l/2}, \ldots, m_t, \ldots, m_{t+l/2}). \quad (8)$$

Accordingly, the example implementation compares two observed patterns of arbitrary length using dynamic time warping (e.g., frame by frame analysis of the talking segments). The first pattern is transformed into the second pattern by either transforming a first mouth configuration into a second mouth configuration, or by allowing insertions or deletions in the first out configuration. As noted above, the cost for direct transformation operations is $msim_{norm}$ between the two transformed mouth configurations, maximum-normalized to [0, 1]. A greater dissimilarity is associated with a higher cost. Further, insertion and deletion operations are assigned the maximum cost of 1. Because the same mouth motion may not always be performed at the same speed, temporal warping using insertions and deletions provides for matching of similar patterns having different lengths. As a result, the overall pattern match cost is the cost sum of the optimal sequence of transformation operations.

To find possible repetitions, reference patterns around locally unique mouth configurations are extracted. For example, the maxima in $d_w(t)$ may be extracted. Then, a search is performed for matching patterns that are in the direct vicinity, such as plus or minus 5 seconds, for example but not by way of limitation, that have a match cost that is below a threshold $\tau_{match}$.

Figure 3A:
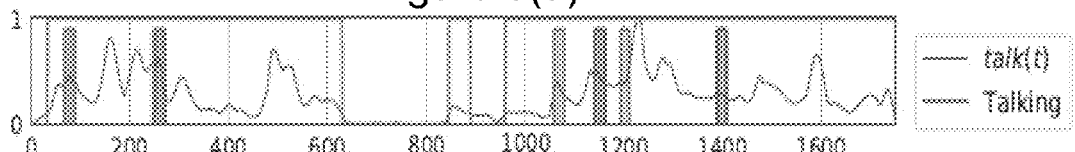
FIGS. 3(a)-3(b) illustrate a comparison of repeating mouth patterns for a person with aphasia and a control group member, as determined according to an example implementation.
Figure 3B:
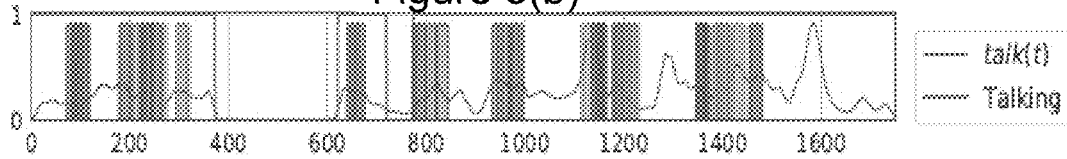

FIGS. 3(a) and 3(b) respectively illustrate examples for pattern matches, for a patient with aphasia that frequently repeat single words, as compared with a person without aphasia. Although repeating patterns exist in both cases, the patient with aphasia demonstrates few but direct repetitions, compared to the many highly interleaved repetitions for the person without aphasia. Accordingly, direct repetitions that are separated by none or a few other patterns can be indicative of direct word repetitions, such that occurrences of direct repetitions are counted and normalized by the total talking time, to obtain a measure of visual repetitions per second, as an indicator of aphasia. The foregoing operations are performed as instructions stored in a storage and executed as operations on a processor, such as a GPU or CPU.

In addition to detecting patterns that occur or repeat within a time window, patterns may be collected over a complete video, to assess variety of speech, which directly correlates to variety in mouth motion or expression, and thus, to actual variety in speech. For example, a person capable of only expressing a few words or utterances which show less variety in mouth motion, as compared with an unimpaired person having a normal vocabulary.

According to an example implementation, this approach of considering a longer time window, and assessing whether there are clusters across the entire speech event, such as a telephone conversation or a video conference, a diagnostic of the vocabulary being used by the patient can be performed without knowing the identity of the actual words in the speech. This is done by obtaining a measure of vocabulary variety, as explained herein.

More specifically, a measure of vocabulary variety is obtained by building a visual vocabulary of mouth patterns for each person, by collecting a fixed number of patterns throughout a video, and aggregating the patterns, using clustering, with a fixed number of clusters. The patterns that repeat at least once are selected. However, as would be understood by those skilled in the art, a different threshold may be selected, such as repeating twice, or some other value of pattern repetition.

The representatives of all cluster centers form the vocabulary. According to the example implementation, k-medioids clustering is used, with a predefined vocabulary size k. However, other clustering heuristics may be substituted therefor without departing from the inventive scope of the example implementation. For a small vocabulary size k, a measurement is performed to determine how well the represents the complete variety of mouth motion of the patient. The talking in the video are divided into fixed sized blocks of mouth motion. Each of the blocks has the same length as the patterns in the vocabulary. Each block is assigned the vocabulary element with the lowest pattern match cost, as explained above with respect to repetitive pattern determination. Thus, the complete mouth motion is reconstructed during talking, by only concatenating the best fitting vocabulary elements. Based on this reconstruction, a measurement is obtained of the match cost for the reconstruction cost between each block, as well as its assigned pattern. A calculation is then performed of the total reconstruction cost as the blockwise average. The foregoing operations are performed as instructions stored in a storage and executed as operations on a processor, such as a GPU or CPU.

Where there is limited variety in mouth motion, a small vocabulary describes the overall motion sufficiently well, and leads to a good reconstruction. The reconstruction cost is computed for k for each of a plurality of values, and the mean of the reconstruction cost is the final score of mouth motion variety, which is an indicator of aphasia in the patient.

In addition to not detecting the actual semantics of the words in a conversation itself, thus preserving the privacy of the patient with respect to the content of the conversation, the example implementations may also have additional benefits and advantages. As one example of such a benefit, there is no need for the tool or the clinician to understand the grammar of the patient in order to apply the tool. For example, the clinician need not know the language of the patient to treat or study aphasia for one or more patients. Similarly, for broader studies that aggregate information of patients, greater populations may be able to participate in such studies, because there is no requirement for the tool to be language specific. One such additional feature would be that the example implementations are language-agnostic. Thus, the example implementation may be employed, regardless of the language being spoken by the patient.

As explained above, information associated with pauses, repetition and vocabulary size are obtained for the patient. This information associated with pause, repetition and vocabulary size is applied to provide an aggregate prediction with respect to the presence or absence of aphasia, as well as the degree or type of aphasia. While the example implementation is directed to aphasia, other cognitive or speech disorder may also be predicted. A training collection of videos of patients with a given disorder may be provided, along with examples of control patients who do not exhibit the disorder, such that learning techniques can be used, such as machine learning or neural networks or the like, to learn the characteristic combinations of features that are predictive of the presence of the disorder.

In the foregoing example implementations, machine learning may be used to generate predictions that are based on example videos, such as publicly or privately stored videos showing examples of facial activity of one or more patients with aphasia. Use this past data as a basis, the machine learning can be used to generate predictions of aphasia. Generic machine learning tools as would be known by those skilled in the art may be employed. Further, and as also explained herein, decision trees and support vector machines may also be executed as instructions on a non-transitory computer-readable medium have a processor (e.g., CPU or GPU). Further, by using a processor interconnected with the sensor of the patient, such as via a network, the example implementation may be performed independently of language, country, location, etc.

For example, but not by way of limitation, over a video of several minutes, the features can be extracted, along with statistical information of their distributions and generic classifiers, including but not limited to decision trees or support vector machines, which can be applied to learn the separating function between the two classes, namely the patients with the given disorder and the control patients.

Figure 4:
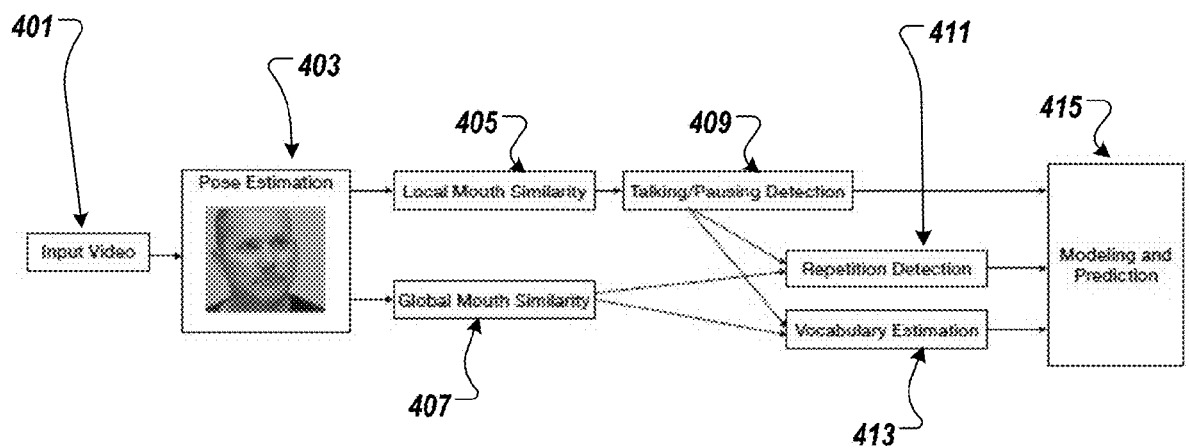
FIG. 4 illustrates an example system diagram according to an example implementation.

FIG. 4 illustrates an example system diagram 400 associated with the example implementations. According to the example system 400, an input video is provided at 401. At 403, pose estimation is performed, so as to produce local mouth similarity at 405, and global mouth similarity at 407. At 409, the local mouth similarity generated at 405 is input, to perform detection of pause frequency. At 411, a result of the pause frequency detection at 409, as well as the global mouth similarity provided at 407, are provided as inputs, to determine the presence of repetitive patterns. Further, at 413, the result of the pause frequency detection at 409 and the global mouth similarity generated at 407 are provided as inputs, to who provide a visual clustering determination of vocabulary patterns to assess mouth motion variety, as explained above. At 415, outputs of the pause determination, repetition detection and visual vocabulary pattern recognition are input to a modeling and prediction tool, which performs the aggregation and prediction with respect to the presence or absence of aphasia, as explained above.

Figure 5:
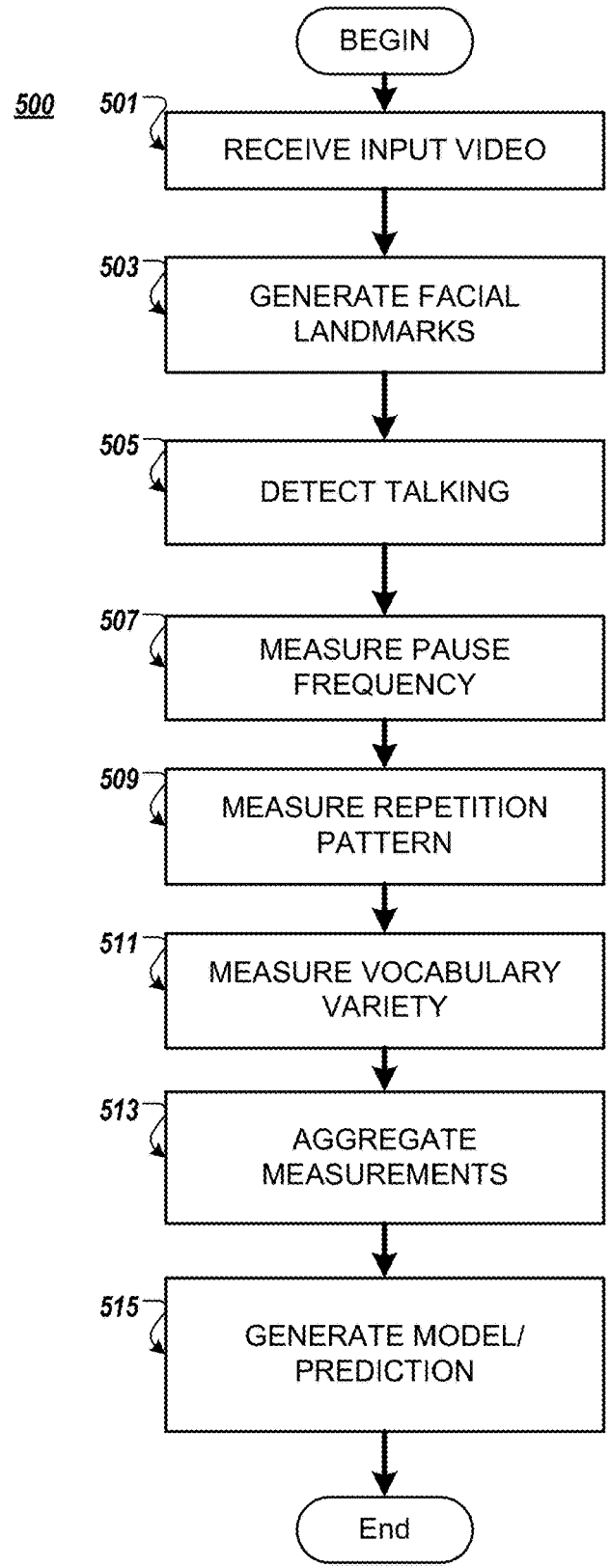
FIG. 5 illustrates an example process according to an example implementation.

FIG. 5 illustrates an example process 500 according to the example implementations. The example process 500 may be performed on one or more devices, as explained here.

At 501, an input video is received. For example, but not by way of limitation, the input video may be generated outside of a clinical setting by a patient, such as during a video conference. The patient may be using a mobile communication device, such as a smartphone, laptop, tablet, or other device, integral or separable, that includes an input device such as a camera. The example implementations are not limited to a video camera, and any other sensing device that can perform a function of sensing the facial region of the patient may be substituted therefor. For example, but not by way of limitation, a 3-D camera may be used to sense features of a face, and generate a signal for processing according to the example implementations.

It is not required for the input device to include a microphone for the purpose of the present example implementation because audio or other speech semantic output is not analyzed. Optionally, the patient may also receive an input from another user with whom he or she is communicating, such as a video screen and/or audio output such as speaker or headphone. For the purpose of the example implementations, the activity of the patient is captured by an input device, and the input is transmitted to one or more processors, such as a server, which receives the input video.

At 503, the input video is used to generate a facial landscape of the patient. As explained above, characteristic facial points are determined, and a subset of the characteristic facial points associated with the mouth is identified as the facial points of focus.

At 505, a determination is made as to whether the facial motion in the input video is talking. As explained above, non-talking movement of the subset of facial points (e.g., jitter, nodding, shaking) are filtered out, and a closing operation is performed to obtain a talk score, which indicates a period of talking.

At 507, for the period of talking, pause frequency is measured. For example, but not by way of limitation, areas of inactivity within the talking instances obtained in 505 may be measured as pauses, and a frequency of the measured pauses is determined.

At 509, patterns of repetition are determined. More specifically, based on a pattern of mouth motion, multiple observed patterns are measured for similarity. The occurrence of direct repetition is measured and normalized by the total talking time, to obtain a measure of visual repetitions per second, for example.

At 511, overall variety in mouth motion is measured, to determine vocabulary variety, without identifying the content of the vocabulary. Mouth patterns and clustering is implemented to calculate a final score of mouth motion variety.

At 513, the measurements and scoring obtain from 507 for pause frequency, 509 for patterns of repetition, and 511 for vocabulary variety, are combined (e.g., aggregated).

At 515, the aggregated measurements and scoring are applied to generate a model that is indicative of whether the patient has the medical condition (e.g., aphasia). For example, a training collection of videos may be used to learn the characteristic combinations of features for a medical condition, as explained above.

Figure 6:
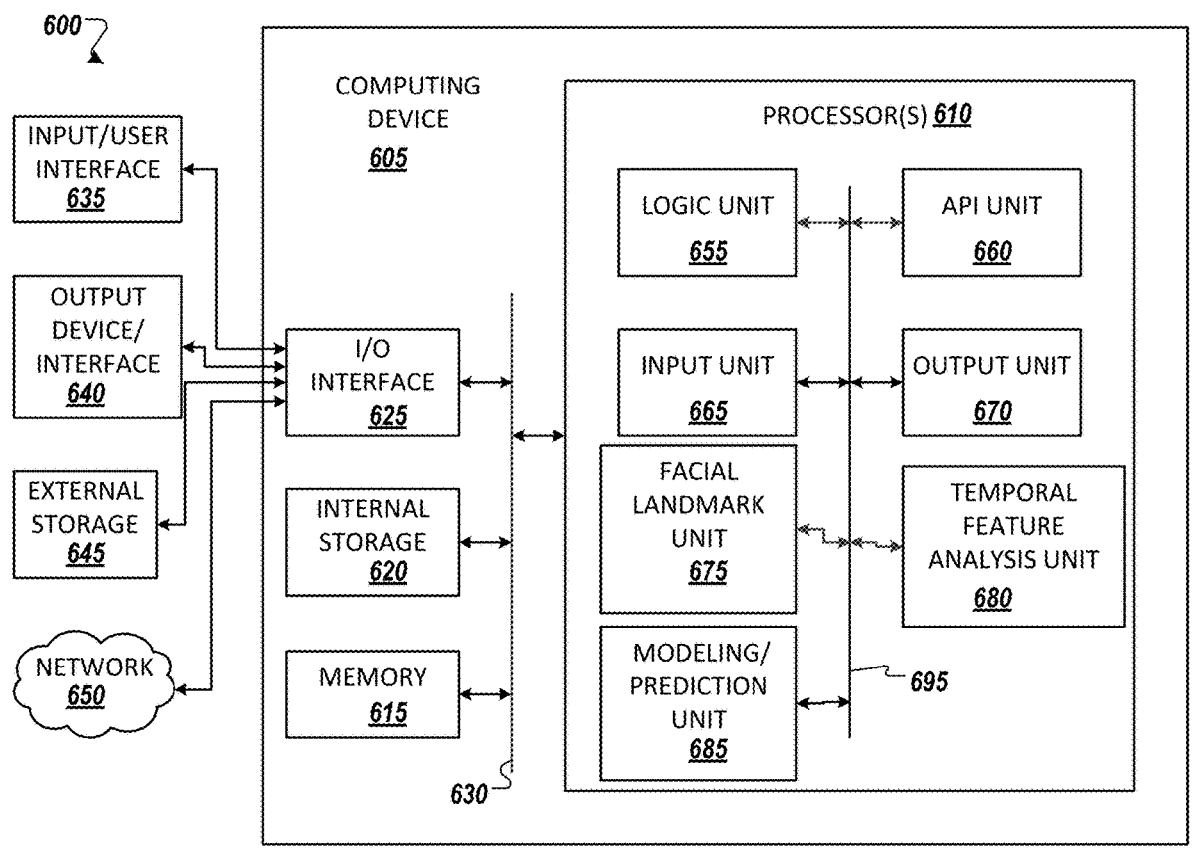
FIG. 6 illustrates an example computing environment with an example computer device suitable for use in some example implementations.

FIG. 6 illustrates an example computing environment 600 with an example computer device 605 suitable for use in some example implementations. Computing device 605 in computing environment 600 can include one or more processing units, cores, or processors 610, memory 615 (e.g., RAM, ROM, and/or the like), internal storage 620 (e.g., magnetic, optical, solid state storage, and/or organic), and/or I/O interface 625, any of which can be coupled on a communication mechanism or bus 630 for communicating information or embedded in the computing device 605.

Computing device 605 can be communicatively coupled to input/interface 635 and output device/interface 640. Either one or both of input/interface 635 and output device/interface 640 can be a wired or wireless interface and can be detachable. Input/interface 635 may include any device, component, sensor, or interface, physical or virtual, which can be used to provide input (e.g., buttons, touch-screen interface, keyboard, a pointing/cursor control, microphone, camera, braille, motion sensor, optical reader, and/or the like).

Output device/interface 640 may include a display, television, monitor, printer, speaker, braille, or the like. In some example implementations, input/interface 635 (e.g., user interface) and output device/interface 640 can be embedded with, or physically coupled to, the computing device 605. In other example implementations, other computing devices may function as, or provide the functions of, an input/interface 635 and output device/interface 640 for a computing device 605.

Examples of computing device 605 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, server devices, other computers, information kiosks, televisions with one or more processors embedded therein and/or coupled thereto, radios, and the like).

Computing device 605 can be communicatively coupled (e.g., via I/O interface 625) to external storage 645 and network 650 for communicating with any number of networked components, devices, and systems, including one or more computing devices of the same or different configuration. Computing device 605 or any connected computing device can be functioning as, providing services of, or referred to as, a server, client, thin server, general machine, special-purpose machine, or another label. For example but not by way of limitation, network 650 may include the blockchain network, and/or the cloud.

I/O interface 625 can include, but is not limited to, wired and/or wireless interfaces using any communication or I/O protocols or standards (e.g., Ethernet, 802.11xs, Universal System Bus, WiMAX, modem, a cellular network protocol, and the like) for communicating information to and/or from at least all the connected components, devices, and network in computing environment 600. Network 650 can be any network or combination of networks (e.g., the Internet, local area network, wide area network, a telephonic network, a cellular network, satellite network, and the like).

Computing device 605 can use and/or communicate using computer-usable or computer-readable media, including transitory media and non-transitory media. Transitory media includes transmission media (e.g., metal cables, fiber optics), signals, carrier waves, and the like. Non-transitory media includes magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computing device 605 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C #, Java, Visual Basic, Python, Perl, JavaScript, and others).

Processor(s) 610 can execute under any operating system (OS) (not shown), in a native or virtual environment. One or more applications can be deployed that include logic unit 655, application programming interface (API) unit 660, input unit 665, output unit 670, facial landmark unit 675, temporal feature analysis unit 680, modeling/prediction unit 685, and inter-unit communication mechanism 695 for the different units to communicate with each other, with the OS, and with other applications (not shown).

For example, the facial landmark unit 675, the temporal feature analysis unit 680, and the modeling/prediction unit 685 may implement one or more processes shown above with respect to the structures described above. The described units and elements can be varied in design, function, configuration, or implementation and are not limited to the descriptions provided.

In some example implementations, when information or an execution instruction is received by API unit 660, it may be communicated to one or more other units (e.g., logic unit 655, input unit 665, facial landmark unit 675, temporal feature analysis unit 680, and modeling/prediction unit 685).

For example, the facial landmark unit 675 may receive and process an input video, and register 2D landmarks on an image of a face of a patient, to generate a model of characteristic facial points, as explained in greater detail above. An output of the facial landmark unit 675 is provided to the temporal feature analysis unit 680, which performs analysis to detect talking, pause frequency, repetitive patterns, and visual vocabulary of mouth patterns, as explained in greater detail above. An output of the temporal feature analysis unit 680 is provided to the modeling/prediction unit 685, which generates a model, and provides an inference with respect to the patient's condition with respect to a presence or absence of a medical condition such as aphasia.

In some instances, the logic unit 655 may be configured to control the information flow among the units and direct the services provided by API unit 660, input unit 665, facial landmark unit 675, temporal feature analysis unit 680, and modeling/prediction unit 685 in some example implementations described above. For example, the flow of one or more processes or implementations may be controlled by logic unit 655 alone or in conjunction with API unit 660.

Figure 7:
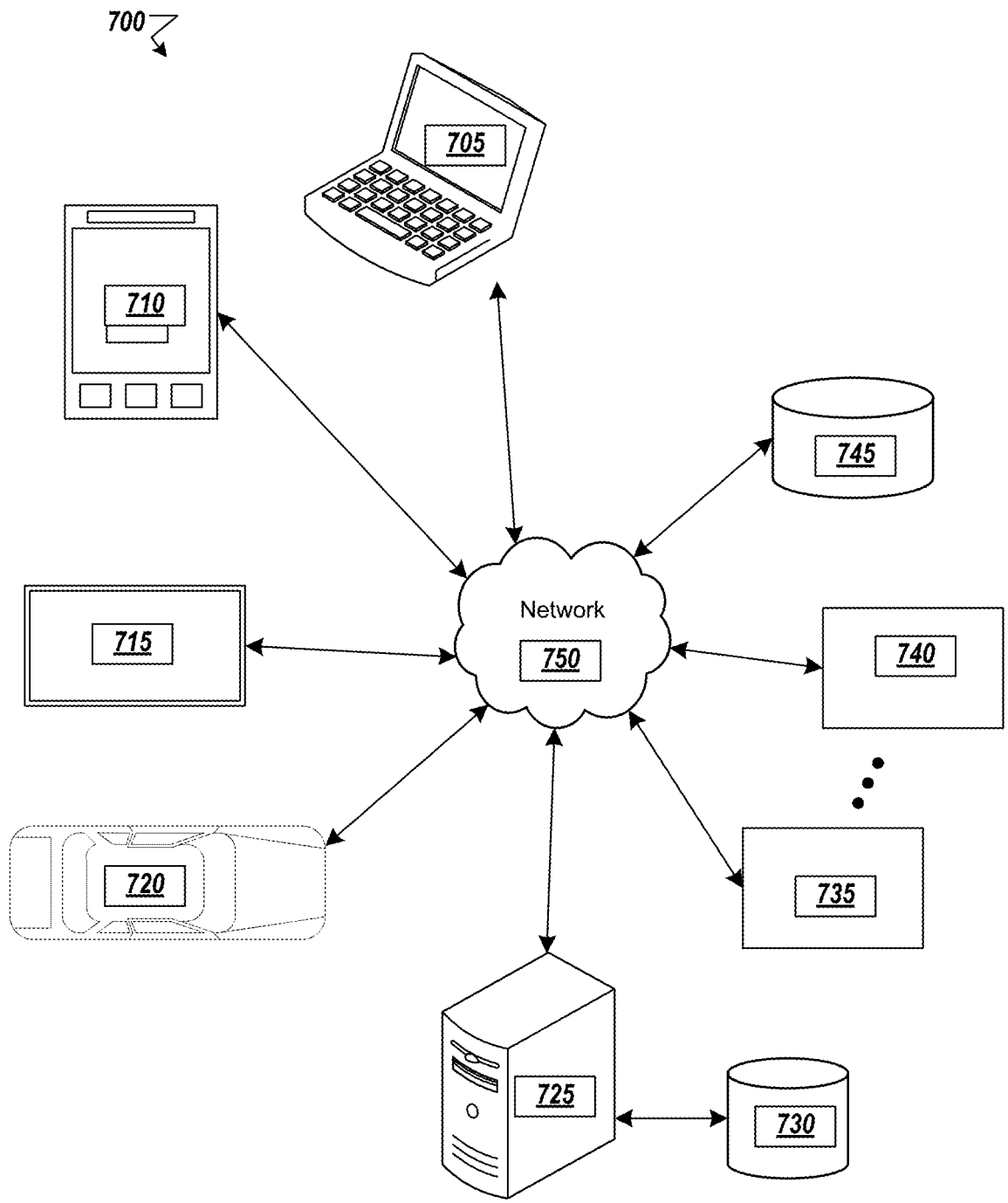
FIG. 7 shows an example environment suitable for some example implementations.

FIG. 7 shows an example environment suitable for some example implementations. Environment 700 includes devices 705-745, and each is communicatively connected to at least one other device via, for example, network 760 (e.g., by wired and/or wireless connections). Some devices may be communicatively connected to one or more storage devices 730 and 745.

An example of one or more devices 705-745 may be computing devices 605 described in FIG. 6, respectively. Devices 705-745 may include, but are not limited to, a computer 705 (e.g., a laptop computing device) having a monitor and an associated webcam as explained above, a mobile device 710 (e.g., smartphone or tablet), a television 715, a device associated with a vehicle 720, a server computer 725, computing devices 735-740, storage devices 730 and 745.

In some implementations, devices 705-720 may be considered user devices associated with the users of the enterprise. Devices 725-745 may be devices associated with service providers (e.g., used by the external host to provide services as described above and with respect to the various drawings, and/or store data, such as webpages, text, text portions, images, image portions, audios, audio segments, videos, video segments, and/or information thereabout).

While the foregoing example implementations are directed to aphasia, any other disorder that is indicated by movement of the facial points may also be modeled and predicted, as explained above. For example, but not by way of limitation, in a medical facility or a home of the patient at high risk for a condition, cameras may be installed that use computer vision to obtain the facial points and perform an analysis on the relevant subset of the facial points, to attack the presence of a condition. In some conditions, such as a stroke, certain facial activity may occur prior to other detectable activity, as an advance indication of a potential life-threatening event, such as a stroke. Having one or more cameras that is able to detect such facial point movement at an early stage may be used to aid in early detection, and obtain early treatment for a potential patient of a stroke. Such a tool may be installed in integration with a network, a localized security system, mobile devices associated with the user having cameras, or even objects in the room that a user may be paying attention to, such as a television or display screen.

According to another example implementation, an online application for speech therapy may use the implementations described herein. For example, not by way of limitation, a user may use a speech therapy application, downloaded onto a device, such as a tablet, laptop, television, smart phone or other device, wherein a video camera is present, such that the user may obtain feedback on their conditions. Further, a user that is engaging in therapeutic activity based on instructions, either from clinician or the online application itself, may use the tool to track progress, and receive further feedback on additional therapy or relevant medical information.

Further, the example implementations may be integrated into a communication application between the patient and one or more other users, such as a teleconference or videoconference system. In such a system, the online application may use the example implementations, as a third-party tool or an integrated tool or add-in, for the patient to self-assess aphasia while in communication with others. This may also be beneficial to the patient, in that if the patient is having conditions of aphasia that are presenting, they may adjust their communication schedule, track progress or the like. On the other hand, the user other than the patient that is in communication with the patient may be provided, with the consent of the patient information that the patient has aphasia, to avoid potential frustration, embarrassment or awkward situations between the patient and the other user.

It is also noted that the foregoing act example implementations may be used in combination with a related art audio system that also performs detection of the content of the speech. However, the related art audio system is not required for the example implementation, and as explained above, the example implementation may be used without any audio system or other system that would provide privacy preserving information to another party.

At a broader study level, analytics associated with aphasia may be used to recognize patterns across large numbers of patients. Pattern recognition of when and how symptoms manifest, such as due to a certain trigger or after a certain amount of time, may be useful to determine and assess a degree or type of aphasia. Such information may be used in large-scale studies, with the consent of the patient.

The foregoing example implementations may have various benefits and advantages over the related art. For example, but not by way of limitation, according to the example implementations, the privacy of the patient is preserved while permitting the determination and prediction with respect to whether the patient has aphasia, as well as the severity of aphasia. Further, as also explained above, the example implementation is language agnostic, and can be adopted over multiple differing languages without requiring modification. Further, the example implementation permits the recognition of speech properties without revealing the content of the speech itself, and focusing on temporal features of facial motion to in for properties of speech pattern, without detecting or determining the actual speech content.

Although a few example implementations have been shown and described, these example implementations are provided to convey the subject matter described herein to people who are familiar with this field. It should be understood that the subject matter described herein may be implemented in various forms without being limited to the described example implementations. The subject matter described herein can be practiced without those specifically defined or described matters or with other or different elements or matters not described. It will be appreciated by those familiar with this field that changes may be made in these example implementations without departing from the subject matter described herein as defined in the appended claims and their equivalents.

What is claimed is:

1. A computer-implemented method of assessing whether a patent has a condition, comprising:
   generating a facial landmark on a received input video to define points associated with a region of interest on a face of the patient;
   defining a period of talking based respective positions of the defined points;
   during the period of talking, measuring pause frequency, repetitive pattern, and vocabulary variety, without determining or applying semantic information associated with the talking, to generate an aggregate score; and
   based on the aggregate score, generating a prediction of the patient having the condition associated with the aggregate score.

2. The method of claim 1, wherein the generating the facial landmark comprises defining, for the region of interest comprising the mouth of the patient, the defined points outlining the lips of the patient, and measuring, over time, a temporal similarity measure of the defined points, and removing body movement and head movement from the temporal similarity measure to generate a temporal dissimilarity measure for the mouth.

3. The method of claim 2, the defining the period of talking comprising filtering out mouth movement associated with jitter and out-of-plane rotations of the mouth, measuring a vertical distance between an upper lip and a lower lip of the lips, and performing a closing operation to generate a talk score indicative of the period of talking.

4. The method of claim 3, the measuring the pause frequency comprising applying a threshold to the talk score, and registering periods of talk inactivity during the period of talking as the pause frequency.

5. The method of claim 1, the measuring the repetitive pattern comprising defining first and second patterns of mouth motion during the period of talking having a length around respective first and second time intervals, and performing a dissimilarity comparison to obtain a number of repetitions over a time period.

6. The method of claim 1, the measuring the vocabulary variety comprising collecting and aggregating a fixed number of vocabulary patterns throughout the input video using clustering with a fixed number of clusters by selecting repeating ones of the patterns, reconstructing the mouth motion over the fixed number of vocabulary patterns to generate a reconstruction cost indicative of a score of mouth motion variety.

7. The method of claim 6, wherein the vocabulary variety is measured without identifying a language of the vocabulary.

8. The method of claim 1, the generating the prediction further comprising applying a decision tree or a support vector machine to learn a separating function between the patient having the condition and the patient not having the condition.

9. A server capable of determining a condition of a patient, the server configured to perform the operations of:
receiving an input video, and performing a facial landmark generation operation on the received input video to define points associated with a region of interest;
defining a period of talking based respective positions of the points associated with the region of interest;
during the period of talking, measuring pause frequency, repetitive pattern, and vocabulary variety, without determining or applying semantic information associated with the talking; and
aggregating the measuring to generate a prediction of the patient having the condition.

10. The server of claim 9, wherein the generating the facial landmark comprises defining, for the region of interest comprising the mouth of the patient, the defined points outlining the lips of the patient, and measuring, over time, a temporal similarity measure of the defined points, and removing body movement and head movement from the temporal similarity measure to generate a temporal dissimilarity measure for the mouth.

11. The server of claim 10, the defining the period of talking comprising filtering out mouth movement associated with jitter and out-of-plane rotations of the mouth, measuring a vertical distance between an upper lip and a lower lip of the lips, and performing a closing operation to generate a talk score indicative of the period of talking.

12. The server of claim 11, the measuring the pause frequency comprising applying a threshold to the talk score, and registering periods of talk inactivity during the period of talking as the pause frequency.

13. The server of claim 9, the measuring the repetitive pattern comprising defining first and second patterns of mouth motion during the period of talking having a length around respective first and second time intervals, and performing a dissimilarity comparison to obtain a number of repetitions over a time period.

14. The server of claim 9, the measuring the vocabulary variety comprising collecting and aggregating a fixed number of vocabulary patterns throughout the input video using clustering with a fixed number of clusters by selecting repeating ones of the patterns, reconstructing the mouth motion over the fixed number of vocabulary patterns to generate a reconstruction cost indicative of a score of mouth motion variety.

15. The server of claim 14, wherein the vocabulary variety is measured without identifying a language of the vocabulary.

16. The server of claim 9, the generating the prediction further comprising applying a decision tree or a support vector machine to learn a separating function between the patient having the condition and the patient not having the condition.

17. A non-transitory computer readable medium having a storage that stores instructions executed by a processor, the instructions comprising:
receiving an input video of a patient, and performing a facial landmark generation operation on the received input video to define points associated with a region of interest;
defining a period of talking based respective positions of the points associated with the region of interest;
during the period of talking, measuring pause frequency, repetitive pattern, and vocabulary variety, without determining or applying semantic information associated with the talking; and
aggregating the measuring to generate a prediction of the patient having a condition associated with the measurements.

18. The non-transitory computer readable medium of claim 17, wherein the generating the facial landmark comprises defining, for the region of interest comprising the mouth of the patient, the defined points outlining the lips of the patient, and measuring, over time, a temporal similarity measure of the defined points, and removing body movement and head movement from the temporal similarity measure to generate a temporal dissimilarity measure for the mouth,
the defining the period of talking comprising filtering out mouth movement associated with jitter and out-of-plane rotations of the mouth, measuring a vertical distance between an upper lip and a lower lip of the lips, and performing a closing operation to generate a talk score indicative of the period of talking,
the measuring the pause frequency comprising applying a threshold to the talk score, and registering periods of talk inactivity during the period of talking as the pause frequency,
the measuring the repetitive pattern comprising defining first and second patterns of mouth motion during the period of talking having a length around respective first and second time intervals, and performing a dissimilarity comparison to obtain a number of repetitions over a time period, and
the measuring the vocabulary variety comprising collecting and aggregating a fixed number of vocabulary patterns throughout the input video using clustering with a fixed number of clusters by selecting repeating ones of the patterns, reconstructing the mouth motion over the fixed number of vocabulary patterns to generate a reconstruction cost indicative of a score of mouth motion variety.

19. The non-transitory computer readable medium of claim 18, wherein the vocabulary variety is measured without identifying a language of the vocabulary.

20. The non-transitory computer readable medium of claim 17, further comprising generating the prediction by applying a decision tree or a support vector machine to learn a separating function between the patient having the condition and the patient not having the condition.

* * * * *